("12") United States Patent  
Redlingshöfer et al.

(10) Patent No.: US 7,592,288 B2
(45) Date of Patent: Sep. 22, 2009

(54) CATALYST FOR THE SYNTHESIS OF ALKYL MERCAPTAN AND PROCESS FOR THE PRODUCTION THEREOF

(75) Inventors: Hubert Redlingshöfer, Münchsteinach (DE); Christoph Weckbecker, Gründau-Lieblos (DE); Andreas Dörflein, Langen (DE); Michael Rückriegel, Biebergemünd (DE)

(73) Assignee: Evonik Degussa GmbH, Essen (DE)

( * ) Notice: Subject to any disclaimer, the term of this patent is extended or adjusted under 35 U.S.C. 154(b) by 608 days.

(21) Appl. No.: 10/923,085

(22) Filed: Aug. 23, 2004

(65) Prior Publication Data

US 2005/0080295 A1 Apr. 14, 2005

(30) Foreign Application Priority Data

Aug. 23, 2003 (DE) ................................ 103 38 887

(51) Int. Cl.
*B01J 23/00* (2006.01)
*B01J 23/02* (2006.01)
*B01J 23/08* (2006.01)
*C01G 41/02* (2006.01)
*C01D 1/02* (2006.01)

(52) U.S. Cl. ....................... 502/317; 502/344; 502/355; 423/594.13; 423/594.15

(58) Field of Classification Search ............. 568/61–73; 502/317, 344, 355; 423/594.13, 594.15
See application file for complete search history.

(56) References Cited

U.S. PATENT DOCUMENTS 2,820,062 A    1/1958  Folkins et al.
5,852,219 A *  12/1998 Sauer et al. ................... 568/71

FOREIGN PATENT DOCUMENTS

EP    0 832 687 A   4/1998

OTHER PUBLICATIONS

Laruelle et al., "High-Energy Milling of WO3 oxides: Amorphization and Reaction with Cs2CO3," Journal of Solid State Chemistry, p. 172-177, (1994).
Kudo et al., "Hexagonal and pyrochlore-type cesium tungstates synethesized from cesium peroxo-polytungstate and their intercalation chemistry," Solid State Ionics, p. 204-208, (1994).
Zhong et al., "Electrochromic properties of cesium tungstate with pyrochlore structure," Thin Solid Films, p. 85-88, (1991).
Mashkina et al., "Activity of tungstate catalysts in the synthesis of methyl-mercaptane from methanol and hydrogen sulfide," Reaction Kinetics and Catalysis Letters, p. 159-164, (1988).

* cited by examiner

*Primary Examiner*—Steven Bos
*Assistant Examiner*—Anthony J Zimmer
(74) *Attorney, Agent, or Firm*—Pillsbury Winthrop Shaw Pittman LLP

(57) ABSTRACT

The invention relates to an oxidic catalyst containing cesium and tungsten for the synthesis of alkyl mercaptans from alkanols and hydrogen sulfide, and to a process for the production of this catalyst, wherein the molar ratio of cesium to tungsten is <2:1.

13 Claims, No Drawings

CATALYST FOR THE SYNTHESIS OF ALKYL MERCAPTAN AND PROCESS FOR THE PRODUCTION THEREOF

PRIORITY CLAIM

This application claims benefit under 35 U.S.C. § 119 to German Application No. 103 38 887.7, filed Aug. 23, 2003.

FIELD OF THE INVENTION

The present invention relates to an oxidic catalyst containing cesium and tungsten for the synthesis of alkyl mercaptans from alkanols and hydrogen sulfide, and to a process for the production of this catalyst.

BACKGROUND OF THE INVENTION

Methyl mercaptan in particular is an industrially important intermediate., e.g. for the synthesis of methionine as well as for the synthesis of dimethyl sulfoxide and dimethylsulfone. Today, it is produced predominantly from methanol and hydrogen sulfide by reaction on a catalyst of aluminum oxide. The synthesis of the methyl mercaptan generally takes place in the gas phase at temperatures of between 300 and 500° C. and under pressures of between 1 and 25 bar.

Apart from the methyl mercaptan formed, the reaction mixture contains the unreacted starting substances and by-products, such as e.g. dimethyl sulfide and dimethyl ether, as well as the gases that are inert in the context of the reaction, such as e.g. methane, carbon monoxide, hydrogen and nitrogen. The methyl mercaptan formed is separated from this reaction mixture.

For the economic efficiency of the process, the highest possible selectivity is demanded in the catalytic reaction of methanol and hydrogen sulfide to form methyl mercaptan, in order to keep the costs as low as possible for the separation of the methyl mercaptan formed from the reaction mixture. A major cost factor here is represented in particular by the energy input for cooling the reaction gas mixture to condense the methyl mercaptan.

To increase activity and selectivity, potassium tungstate or cesium tungstate is conventionally added to aluminum oxide as the support. The tungstate is generally used in quantities of up to 25 wt. %, based on the total weight of the catalyst. An improvement in activity and selectivity is also obtained by increasing the molar ratio of hydrogen sulfide to methanol. Molar ratios of between 1 and 10 are conventionally used.

However, a high molar ratio also means a high excess of the hydrogen sulfide in the reaction mixture and thus the need to circulate large quantities of gas. To reduce the energy input required for this, the ratio of hydrogen sulfide to methanol should therefore deviate from 1 only slightly.

U.S. Pat. No. 2,820,062 relates to a process for the production of organic thiols, in which a catalyst of active aluminum oxide is used, to which potassium tungstate has been added in a quantity of 1.5 to 15 wt. %, based on the weight of the catalyst. With this catalyst, good activities and selectivities are achieved at reaction temperatures of 400° C. and molar ratios of 2. This US Patent Specification mentions various ways of introducing the potassium tungstate into the aluminum oxide. Thus, impregnation processes, co-precipitations and pure mixings are mentioned as being applicable. Little importance is attached to the actual production of the catalyst for the economic efficiency of the process for methyl mercaptan synthesis.

In EP 0 832 687 B1, the advantages of using cesium tungstate ($Cs_2WO_4$) instead of potassium tungstate ($K_2WO_4$) as promoter are described. Thus, by using cesium tungstate, increased activity can be achieved with good selectivity at the same time.

By increasing the cesium tungstate concentration to up to 40 wt. %, the selectivity towards methyl mercaptan can be increased to up to 92% without the activity being disproportionately impaired.

According to the general opinion, the best selectivity is achieved with catalysts in which the alkali/tungsten ratio equals 2:1 (A. V. Mashkina et al., React. Kinet. Catal. Lett., vol. 36, No. 1, 159-164 (1988)).

SUMMARY OF THE INVENTION

The object of the present invention is to provide a catalyst and a process for the production thereof, which is distinguished by improved activity and selectivity with low molar ratios of hydrogen sulfide to methanol compared with the known catalysts, and thus leads to better economic efficiency of the process.

This object is achieved by the provision of a catalyst containing a catalytically active oxidic composition of cesium and tungsten with a molar ratio of cesium to tungsten of <2:1, particularly <2:1 to 0.8:1, preferably 1.9:1 to 1:1, especially 1.6:1 to 1:1.

DETAILED DESCRIPTION OF THE INVENTION

The oxidic composition can be described by the formula $Cs_xWO_y$, in which x signifies <2 to 0.8 and y signifies 3.4 to <4.

The catalyst contains this composition in a quantity of 15 to 45 wt. %, particularly 20 to 36 wt. %, preferably >25 to 36 wt. %. In the case of a core-shell catalyst, these proportions relate to the composition of the shell.

The composition of cesium and tungsten can be impregnated directly on to a support body to produce the catalyst in the form of a supported catalyst. In the production of catalysts in the form of extrudates or pellets, the powdered support is impregnated or mixed with the oxidic composition and the intermediate obtained is then shaped. If a core-shell catalyst is being produced, the powdered support is impregnated with the catalytically active composition and the resulting mixture is then applied on to an inert support core in the form of a shell.

The support materials can also contribute to the catalytic activity in individual cases.

The Cs/W ratio is preferably <1.9:1 to 1:1. Thus, the catalysts according to the invention for the reaction of alkanols with hydrogen sulfide to form alkyl mercaptans contain a hyperstoichiometric proportion of tungsten compared with the catalyst from the prior art impregnated with cesium tungstate ($Cs_2WO_4$).

It is clear that this higher proportion on the preferably used aluminum oxide imparts improved activity and, at the same time, improved selectivity to the catalyst compared with the stoichiometric alkaline earth or alkali tungstate exclusively used in the prior art. Whereas increasing the concentration of cesium tungstate ($Cs_2WO_4$) causes an increase only in the selectivity of the catalyst with, at the same time, lower activity, when exclusively the tungsten content is increased and the cesium content is unchanged, a further increase in selectivity is unexpectedly demonstrated with, at the same time, increased activity.

According to the invention, excellent selectivity can be achieved with very high loadings with the promoter, without the activity of the catalyst decreasing, as known from the prior art. Furthermore, it has been found that the activity and selectivity of the catalyst can be adjusted in a targeted manner by means of the alkali-tungsten ratio. The catalyst is used in the form of a supported catalyst, in which the surface is impregnated with the catalytically active substance, or a core-shell catalyst, in which a core is surrounded by a mixture of catalytically active substance and support material. Furthermore, extrudates or pellets in which the catalytically active substance is mixed with the powdered support material before being shaped, or the latter is impregnated therewith, can be used (uniform catalyst).

The known oxidic, inorganic compounds are used as support materials for this catalyst, such as e.g. $SiO_2$, $TiO_2$, $ZrO_2$ and preferably so-called active aluminum oxide. This material exhibits high specific surfaces of between about 10 and 400 $m^2$/g and consists mainly of oxides of the transition series of the crystallographic phases of aluminum oxide (cf. e.g. Ullmann's Enzyclopedia of Industrial Chemistry, 1985, vol. A1, pages 561-562). These transition oxides include $\gamma$-, $\delta$-, $\eta$-, $\kappa$-, $\chi$- and $\theta$-aluminum oxide. All these crystallographic phases are converted to the thermally stable $\alpha$-aluminum oxide when the aluminum oxide is heated to temperatures of more than 1100° C. Active aluminum oxide is commercially available for catalytic applications in various grades and physical forms.

Particularly suitable for the production of supported catalysts are formed pieces of granulated or extruded aluminum oxide with particle diameters of 1 to 5 mm, a specific surface of 180 to 400 $m^2$/g, a total pore volume of between 0.3 and 1.2 ml/g and a bulk density of 300 to 900 g/l. For the purposes of the invention, aluminum oxide with more than 200 $m^2$/g specific surface is preferably used, since the catalytic activity of the finished catalyst increases slightly with increasing surface area of the aluminum oxide. This material is used in powdered form, preferably for the production of the core-shell catalysts, extrudates or pellets.

The aqueous impregnating solution for applying the promoter can be simply produced from water-soluble Cs and tungsten compounds, particularly tungstic acid ($H_2WO_4$) and cesium hydroxide ($Cs(OH).H_2O$). For this purpose, for example tungstic acid is suspended in water and dissolved with the addition of a base and heating. Cesium hydroxide or another cesium salt is also dissolved in water and combined with the solution of the tungstic acid (promoter solution). Cesium salts, the anions of which can be driven off completely by heat treatment, such as e.g. nitrates, formates, oxalates, acetates or carbonates, are preferably used. Inorganic and also organic bases are suitable for stabilizing this solution with a pH of 8 to 14.

Those bases that can be driven off completely by a final heat treatment of the catalyst obtained after impregnation are preferably used. These bases include preferably ammonium hydroxide and organic bases, particularly amines. Compared with the prior art, the molar ratio of Cs and W when preparing the aqueous impregnating solution is selected such that, in contrast to cesium tungstate ($Cs_2WO_4$) with a Cs/W ratio of 2 to 1, a higher proportion of tungsten, i.e. a Cs to W ratio of less than 2 to 1, particularly <1.9:1 to 0.8:1, is present. This leads to markedly increased activity and selectivity of the catalysts according to the invention compared with the known catalysts, particularly with low ratios of hydrogen sulfide and methanol in the reaction gas.

For the application of the promoter solution, various impregnating techniques can be used, such as dip impregnation, spray impregnation, vacuum impregnation and pore volume impregnation, it being possible for the impregnation to take place more than once. In the case of formed pieces, the selected impregnating method must enable the desired loading quantity of the promoter to be applied with good uniformity over the entire cross section.

The promoter solution is preferably applied on to the formed pieces in one or two steps by spray or vacuum impregnation. In spray impregnation, the aqueous impregnating solution is sprayed on to the support bodies. In vacuum impregnation, reduced pressure is created using a vacuum pump in a vessel filled with the formed pieces. By opening a hose connection to the aqueous impregnating solution, the solution is sucked into the vessel until the entire charge of formed pieces is covered with the solution. After an impregnating period of 0.2 to 2 hours, the solution not taken up by the material is discharged or poured off.

By pre-drying for a period of 1 to 10 hours at room temperature, the initial concentration gradient over the cross section of the formed pieces can be largely equalized. Thus, the uniformity of the impregnation over the cross section of the catalyst particles is improved. The catalyst precursors thus obtained are preferably dried for a period of 1 to 10 hours at 100 to 200, preferably 100 to 140° C., to remove the residual moisture. A calcination then takes place for a period of 1 to 20, preferably 1 to 5 hours at 300 to 600, preferably 420 to 480° C. As a result, the promoter is fixed on the aluminum oxide and the base from the impregnating solution is destroyed and driven off. A gas stream may optionally flow through the charge of support bodies for the catalyst precursors during the pre-drying, drying and calcining, which improves the removal of the residual moisture and decomposition gases.

The impregnation of the formed pieces can also take place in multiple steps, particularly in two steps.

In a preferred embodiment, the solution used in the first step then contains one to two thirds of the total quantity of cesium and tungsten compounds provided.

In a multiple-step, but particularly a two-step procedure, the precursor obtained in the first step is optionally not calcined.

Otherwise, the same impregnation, drying and calcination program takes place in the second step as described for the one-step process.

This multiple-step impregnation is sensible particularly when high loadings are desired and/or the limited solubility of the promoter mixture does not allow the loading to be performed in one step.

It is also possible to spray the support bodies with the impregnating solution several times during the impregnating operation (step a from claim 11) and to remove portions of the residual moisture between each of these treatment steps at a temperature of up to 120° C. before going on to step b.

In the production of the core-shell catalyst, the powder to be applied as the shell can be calcined before or after coating. For example, this type of catalyst can be produced in accordance with EP-B-0 068 193. The calcination can also take place before and/or after shaping in the production of extrudates or pellets.

For the following examples, the different types of commercial aluminum oxide listed in Table 1 were used.

TABLE 1

Properties of the aluminum oxide used

| | Aluminum oxide I | Aluminum oxide II |
|---|---|---|
| Manufacturer | Rhodia | Alcoa |
| Type | Spheralite 501A | LD 350 |
| Specific surface [m²/g] | 310 | 350 |
| Bulk density [kg/m³] | 690-790 | 590-660 |
| Water absorption [ml/g] | 0.50 | 0.58 |
| Particle diameter [mm] | 2-5 | 1.2-2.4 |
| Loss on ignition 850° C. [wt. %] | 4.5 | 5.6 |

EXAMPLES

Comparative Example 1

150 g aluminum oxide I was impregnated with 21.0 wt. % cesium tungstate ($Cs_{2.0}WO_4$) by means of vacuum impregnation. The details of the procedure were as follows:

To prepare the impregnating solution, 55.7 g of tungstic acid were suspended in 44.5 g water and dissolved by adding 111.4 g of 25% ammonia solution and heating to 50° C. 74.6 g $Cs(OH).H_2O$ were dissolved in 37.3 g water and mixed with the first solution. The solution was then stirred for 48 hours in a covered beaker. The solution was then topped up with 25 g water to a volume of 234 ml.

The aluminum oxide was placed in a glass vessel, which had been evacuated to 150 mbar. By opening a tap, the impregnating solution was sucked into the evacuated glass vessel until the entire charge of formed pieces was covered with the solution. After waiting 15 minutes and letting air into the glass vessel, the solution not taken up by the aluminum oxide flowed back into the beaker. During this operation, 79 ml of impregnating solution were taken up by the aluminum oxide.

The granules were dried for a period of 1 hour at room temperature in an air stream and then at 120° C. for 3 hours to remove the residual moisture. The granules were then calcined for 3 hours at 455° C.

Comparative Example 2

Comparative example 1 was repeated with a 26.3% loading of the aluminum oxides with cesium tungstate ($Cs_{2.0}WO_4$).

Example 1

150 g aluminum oxide I was impregnated with 23.4 wt. % promoter ($Cs_{1.6}WO_y$) by vacuum impregnation.

For this purpose, 71.9 g tungstic acid were suspended in 44.5 g water and dissolved by adding 111.4 g of 25% ammonia solution and heating to 50° C. 76.9 g $Cs(OH).H_2O$ were dissolved in 37.3 g water and mixed with the first solution. The solution was then stirred in a covered beaker for 48 hours. The solution was then topped up with 19 g water to a volume of 234 ml.

Impregnation, drying and calcination were carried out as in preceding examples.

Example 2

150 g aluminum oxide I was impregnated with 25.8 wt. % promoter ($Cs_{1.3}WO_y$) by vacuum impregnation.

For this purpose, 88.9 g tungstic acid were dissolved in 44.5 g water and 177.7 g of 25% ammonia solution. 79.3 g $Cs(OH).H_2O$ were then added and the solution was heated to 50° C. The solution was then stirred in a covered beaker for 67 hours. The solution was then topped up with 5 g water to a volume of 234 ml.

Impregnation, drying and calcination were carried out as in preceding examples.

Example 3

150 g aluminum oxide I was impregnated in a two-step impregnation with a total of 30.5 wt. % promoter ($Cs_{1.0}WO_y$) by vacuum impregnation. The details of the procedure were as follows:

63.3 g tungstic acid were suspended in 50.7 g water and dissolved by adding 126.5 g of 25% ammonia solution and heating to 50° C. 42.4 g $Cs(OH).H_2O$ were dissolved in 21.2 g water and mixed with the first solution. The solution was then stirred in a covered beaker for 66 hours. The solution was then topped up with 40 g water to a volume of 234 ml. The aluminum oxide was placed in a glass vessel that was evacuated to 150 mbar. By opening a tap, the impregnating solution was sucked in until the entire charge of formed pieces was covered with the solution. After waiting for 15 minutes and letting air into the glass vessel, the solution not taken up by the aluminum oxide flowed back into the beaker. During this operation, 76 ml of impregnating solution were taken up by the aluminum oxide. The granules were then dried for 1 hour at room temperature and then at 120° C. for 3 hours, and calcined for 3 hours at 455° C. As a result of this treatment, 18.7 wt. % promoter had been deposited on the catalyst particles.

To perform the second impregnation, an impregnating solution identical to that in the first step was prepared and applied on to the already loaded catalyst from the first step in the same way by vacuum impregnation. This was then followed by drying again for 1 hour at room temperature, followed by a 3-hour drying at 120° C. Finally, the catalyst particles were calcined for 4 hours at 455° C. in air.

Example 4

Example 3 was repeated with a 31.4% loading of the aluminum oxide with cesium tungstate ($Cs_{1.4}WO_y$).

Example 5

Example 3 was repeated with a 34.5% loading of the aluminum oxide with cesium tungstate ($Cs_{1.6}WO_y$).

Example 6

Example 3 was repeated with a 33.2% loading of the aluminum oxide with cesium tungstate ($Cs_{1.4}WO_y$). Instead of the aluminum oxide I, however, aluminum oxide II was used.

Example 7

300 g aluminum oxide I was impregnated with a total of 35.3 wt. % promoter ($Cs_{1.4}WO_y$) by spray impregnation.

To prepare the impregnating solution, 95.1 g tungstic acid were suspended in 76.0 g water and dissolved by adding 190.1 g of 25% ammonia solution and heating to 50° C. 90.2 g CsOH.H₂O were dissolved in 45.1 g water and mixed with the first solution. The solution was then stirred in a covered beaker for 48 hours. The granules were sprayed with the impregnating solution while being rolled round in a coating pan. Since, owing to the limited water absorption, the granules could not take up the entire liquid volume of the impregnating solution, the granules were heated several times to 110° C. with a hot air gun between spraying with the impregnation in order to remove portions of the residual moisture.

The granules were then stored in air for a period of 1 hour and then dried at 120° C. for 3 hours to remove the residual moisture. The granules were then calcined for 3 hours at 455° C.

Example 8

150 g aluminum oxide I was impregnated with 31.1 wt. % promoter ($Cs_{1.4}WO_y$) by vacuum impregnation.

For this purpose, 123.0 g tungstic acid were suspended in 230.0 g of 25% ammonia solution and 116.2 g CsOH.₂O were added. Immediately after heating to 50° C., the still hot impregnating solution was applied on to the aluminum oxide by vacuum impregnation as described in Comparative Example 1.

Drying and calcination were carried out as in previous examples.

Application Example

The catalysts were tested with respect to their performance data in the synthesis of methyl mercaptan from hydrogen sulfide and methanol.

The synthesis was performed in a stainless steel tube with an 18 mm internal diameter and a length of 500 mm. The catalyst bed of 76 ml in each case was fixed in the reaction tube on both sides by inert beds of glass beads. The reaction tube was heated to the reaction temperature of about 320° C. using a double-walled jacket with a thermo oil.

The test conditions can be taken from the following list:

| | |
|---|---|
| GHSV: | 1300 h⁻¹ (based on standard conditions) |
| LHSV: | 0.84 h⁻¹ (based on liquid MeOH) |
| Reaction temperature: | 320° C. |
| Weight ratio H₂S/MeOH: | 1.9 |
| Pressure: | 9 bar |

The reaction mixture with the products methyl mercaptan, dimethyl sulfide and dimethyl ether and with the unreacted starting substances methanol and hydrogen sulfide is analyzed by online gas chromatography.

The results of the measurements can be taken from Table 2. As the results show, the increase in the cesium tungstate ($Cs_{2.0}WO_4$) loading improves the selectivity, but the activity and the yield deteriorate as a result (Comparative Examples 1 and 2).

If the proportion of tungsten in the catalyst is increased in relation to the proportion of cesium, a marked increase in the activity can be seen with, at the same time, improved selectivity. This leads to an increase in yield of up to 13% compared with the prior art. The selectivity can be raised by increasing the tungsten content and by increasing the total loading to more than 30 wt. % up to about 97%, with a simultaneous rise in methanol conversion. In the industrial synthesis of methyl mercaptan, this also leads to considerable cost savings in the separation of the reaction product from unreacted methanol and by-products.

TABLE 2

Test results

| Catalyst | Aluminum oxide | Molar ratio Cs:W | Loading [wt. %] | Methanol conversion [%] | Selectivity [%] | Yield [%] |
|---|---|---|---|---|---|---|
| CE1 | I | 2:1 | 21.0 | 82.4 | 93.3 | 76.9 |
| CE2 | I | 2:1 | 26.3 | 79.5 | 94.7 | 75.2 |
| Ex. 1 | I | 1.6:1 | 23.4 | 85.0 | 94.9 | 80.7 |
| Ex. 2 | I | 1.3:1 | 25.8 | 90.1 | 94.9 | 85.5 |
| Ex. 3*⁾ | I | 1.0:1 | 30.5 | 97.6 | 92.0 | 89.8 |
| Ex. 4*⁾ | I | 1.4:1 | 31.4 | 89.1 | 96.1 | 85.6 |
| Ex. 5*⁾ | I | 1.6:1 | 34.5 | 85.1 | 97.0 | 82.5 |
| Ex. 6*⁾ | II | 1.6:1 | 33.2 | 91.6 | 96.9 | 88.8 |
| Ex. 7*⁾ | I | 1.4:1 | 35.5 | 85.9 | 95.9 | 82.4 |
| Ex. 8 | I | 1.4:1 | 31.1 | 88.6 | 96.2 | 85.2 |

CE1: catalyst according to Comparative Example 1
*⁾multi-step impregnation

What is claimed is:

1. A catalyst composition comprising a catalytically active oxidic composition of cesium and tungsten having a molar ratio of cesium to tungsten of less than or equal to 1.6:1 wherein said catalytically active oxidic composition is supported by an oxidic inorganic support body.

2. A core-shell catalyst having a support core coated with a shell, wherein the shell comprises the catalyst composition according to claim 1.

3. A core-shell catalyst having a support core coated with a shell, wherein the shell comprises a support material impregnated with the catalyst composition according to claim 1.

4. The catalyst composition according to claim 1, wherein the catalyst composition is present on a support material in a substantially uniform manner.

5. A supported catalyst composition comprising a support body and the catalyst composition of claim 1, wherein the surface of the support body has been impregnated with the catalyst composition.

6. The catalyst composition according to claim 1, wherein the molar ratio of cesium to tungsten ranges from less than 1.6:1 to about 0.8:1.

7. The catalyst composition according to claim 6, wherein the ratio ranges from 1.6:1 to about 1:1.

8. A catalyst composition comprising an oxidic composition, wherein the oxidic composition corresponds to the general formula $Cs_xWO_y$ in which
x ranges from about 0.8 to 1.6, and
y ranges from about 3.4 to less than 4.

9. The catalyst composition according to claim 8, wherein the oxidic composition is present in an amount of about 15 to about 45 wt.%.

10. The catalyst composition according to claim 9, wherein the oxidic composition is present in an amount of about 20 to about 36 wt.%.

11. A supported catalyst composition, comprising a support body or a support material that contains the catalyst composition of claim 8.

12. The supported catalyst composition of claim 11, wherein the support body or the support material is aluminum oxide ($Al_2O_3$).

13. The supported catalyst composition of claim 11, wherein the support body or support material has a specific surface ranging from about 180 to about 400 m²/g (BET) and a total pore volume ranging from about 0.3 to about 1.2 ml/g.

* * * * *